| United States Patent [19] | [11] Patent Number: 4,973,749 |
| --- | --- |
| Siegemund et al. | [45] Date of Patent: Nov. 27, 1990 |

[54] PROCESS FOR THE DIMERIZATION OF HEXAFLUOROPROPENE OXIDE

[75] Inventors: Günter Siegemund, Hofheim am Taunus; Manfred Finke, Kelkheim, both of Fed. Rep. of Germany

[73] Assignee: Hoechst Aktiengesellschaft, Frankfurt am Main, Fed. Rep. of Germany

[21] Appl. No.: 463,545

[22] Filed: Jan. 11, 1990

[30] Foreign Application Priority Data

Jan. 14, 1989 [DE] Fed. Rep. of Germany ....... 3901002

[51] Int. Cl.$^5$ ............................................. C07C 59/13
[52] U.S. Cl. ................................................... 562/851
[58] Field of Search ......................................... 562/851

[56] References Cited

FOREIGN PATENT DOCUMENTS 203466 12/1986 European Pat. Off. .
2195345 8/1987 Japan .

*Primary Examiner*—Paul J. Killos

[57] ABSTRACT

A process for the preparation of the dimer of hexafluoropropene oxide (HFPO), in which the HFPO is dimerized in an aprotic polar solvent in the presence of a catalyst mixture, is described. The catalyst mixture is composed of a metal salt of the elements of the 1st transition metal series of the periodic table and of a tertiary diamine. By bringing in a molar ratio of metal salt to tertiary diamine in the range from 2:1 to 1:2, in particular 1:1, the selectivity for the dimeric compound is greatest, with high yields of the dimer being obtained.

17 Claims, No Drawings

PROCESS FOR THE DIMERIZATION OF HEXAFLUOROPROPENE OXIDE

The invention relates to a process for the preparation of the dimer of hexafluoropropene oxide (HFPO).

Disclosed in the literature is the oligomerization of hexafluoropropene oxide leading to acid fluorides of the formula I with broad distribution of molecular weights (n=0 to 30) (Angew. Chemie 97, 164 (1985))

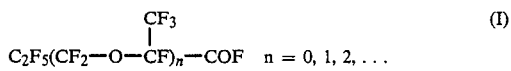

$C_2F_5(CF_2-O-CF)_n-COF \quad n = 0, 1, 2, \ldots$ (I)
(with CF$_3$ branch)

Also already proposed have been catalyst systems which direct the emphasis of the hexafluoropropene oxide oligomerization selectivity to the dimer of the formula I with n=1. Silver nitrate as catalyst in acetonitrile results in this case in a yield of up to 86% of HFPO dimer (DE-A 2 026 669); however, the catalyst is, like most Ag derivatives, sensitive to light and evolves nitrous gases.

The disadvantage of the CuCl/CuCl$_2$/acrylonitrile catalyst system in acetonitrile as solvent, which likewise results in dimeric HFPO in high yield, is the use of acrylonitrile, which is a suspect carcinogen (DE-A 2 924 385).

Furthermore, there are strict requirements on constancy of the temperature during the reaction. It is absolutely necessary to maintain a reaction temperature of $-20°$ C. if cesium fluoride is to act as selective dimerization catalyst for HFPO in the presence of protonic compounds, which is a disadvantage for industrial applications In addition, cesium fluoride is difficult to handle because of its hygroscopic properties, and it represents a very costly catalyst system because part of it is carried out in the oligomer mixture (JP-A 62-195 345).

It has furthermore been disclosed that tertiary amines or N,N-dialkylanilines have a very low catalytic effect even under autogenous pressure (DE-C 1 645 115) and they have been described as inactive (EP-A 0 203 466). Moderate catalysis to dimeric HFPO is elicited only on combination thereof with tetramethylurea.

Hence the object was to find a catalyst system which dimerizes HFPO with high selectivity and simultaneously does not have the disadvantages of the catalyst systems of the state of the art.

The invention relates to a process for the preparation of acid fluorides of the general formula

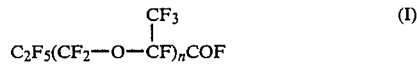

$C_2F_5(CF_2-O-CF)_nCOF$ (I)
(with CF$_3$ branch)

in which n substantially represents the number 1, which is carried out in an aprotic polar solvent in the presence of a catalyst which is composed of a metal salt of the elements of the 1st transition metal series of the periodic table and of a tertiary diamine of the general formula

$R^1R^2N-R-NR^3R^4$ (II)

in which R represents an unbranched or branched, saturated or unsaturated aliphatic hydrocarbon radical which has 1 to 12, preferably 1 to 4, carbon atoms and optionally contains at least one hetero chain member or at least one hetero substituent which is inert toward the reaction components, $R^1$ to $R^4$ are, independently of one another, aliphatic or cycloaliphatic saturated or unsaturated hydrocarbon radicals which have 1 to 12, preferably 1 to 6, carbon atoms and optionally each contain at least one hetero chain member or at least one hetero substituent which is inert toward the reaction components, with, in addition, each two of the radicals $R^1$ to $R^4$ optionally being linked via a hydrocarbon radical or at least on hetero atom.

Hetero substituents, hetero atoms or hetero chain members are groups which generally contain nitrogen or oxygen as hetero atoms.

The statement that n essentially represents the number 1 means that the molecular weight distribution is narrow. Of course, it is also possible for the resulting acid fluorides of the formula (I) to have compositions such that n also represents numbers from zero to 30 besides the number 1; however, only minor amounts of these compounds are formed and they are regarded as impurities.

The advantage of the catalyst system used in the process according to the invention is that it does not have the disadvantages which have been described above and are associated with the state of the art, and represents a system which is superior to the state of the art in terms of the emphasis of the selectivity on the HFPO dimer and of the oligomerization activity. Further advantages are the long useful life of the catalyst and the very low solubility of the catalyst species in the product phase, which permits the catalyst system to be used several times.

A procedure generally selected will be such that initially the metal salt is dissolved in an aprotic polar solvent and subsequently the diamine is added dropwise or in portions, when a color change generally indicates the formation of the catalyst system. Following this, gaseous HFPO is passed in, while stirring and cooling, at a rate such that a desired operating pressure is not exceeded. After the reaction is complete, the product phase is separated off and analyzed. Used as metal salts are fluorides, chlorides, bromides and iodides, as well as cyanides, thiocyanates and acetates of singly, doubly or triply charged metal ions of the 1st transition metal series of the periodic table, specifically of groups Ib, IIb and VIII, for example iron, cobalt, nickel, copper or zinc, preferably CuCl, CuCl$_2$, CoF$_2$, CoCl$_2$ and ZnCl$_2$.

Preferred examples of diamines (II) are tertiary, tetraalkyl-substituted aliphatic diamine compounds with up to 4 carbon atoms in the alkylene group (R) and up to 6 carbon atoms in the alkyl group ($R^1$ to $R^4$) as well as heterocyclic diamines, such as N,N,N',N'-tetramethyl- and -ethylmethylenediamine, N,N,N',N'-tetramethyl-, -ethyl- and -propylethylenediamine, N,N,N',N'-tetramethylpropylene- and -isopropylenediamine, N,N,N',N'-tetramethylhexylidenediamine as well as bis(3-methylpiperidino)-methane and N,N'-dimethylpiperazine. These tertiary diamines (II) are commercially available or can easily be prepared as described in J. Am. Chem. Soc. 73, 3518 (1957) or J. Org. Chem. 52, 467 (1987).

Used as diluents are aprotic polar solvents such as aliphatic and aromatic nitriles having 2 to 8 carbon atoms, aliphatic dinitriles having 5 to 8 carbon atoms and polyglycol dialkyl ethers of the formula R'-(O-CH$_2$-CHR'')$_x$-OR' in which R' denotes an alkyl group having 1 to 4 carbon atoms, R'' denotes hydrogen or methyl and x denotes an integer from 1 to 6, as well as cyclic ethers. Preferred are nitriles or dinitriles such as acetonitrile, propionitrile, butyronitrile, benzonitrile or adipodinitrile as well as ethers such as tetrahydrofuran, dioxane, ethylene and propylene glycol dialkyl ethers, in particular ethylene glycol dimethyl ether and its higher oligomers or mixtures thereof.

The metal salt and the diamine (II) are generally employed in the equimolar molar ratio. The selectivity for the acid fluoride (I) with n=1 is greatest under these conditions. However, less than or more than the stoichiometric amount of diamine (II) compared with the metal salt, with a stoichiometry from 1:2 to 2:1, has only an inconsiderable effect on the desired emphasis on selectivity for the dimeric HFPO.

The concentration of the metal salt/diamine complex in the diluent is generally adjusted in the range of 0.2–1.2 mole of metal salt and 0.2–1.2 mole of diamine per liter of solvent. The activity of the catalyst falls greatly at concentrations below 0.1 mole of metal salt per liter of solvent.

The dimerization of HFPO with the catalysts according to the invention can be carried out in the temperature range from 0° to 50° C., preferably from 5° to 35° C.

The metal salt/diamine (II) catalyst system is active even under atmospheric pressure; however, an elevated pressure in the reaction vessel is preferred in order to make the reaction faster. The pressure in the reaction vessel can be influenced via the rate of inflow of gaseous or liquid HFPO or mixtures thereof. Pressures between 0.5 and 35 bar are used in particular.

The dimer of HFPO can be used for the preparation of perfluorinated propyl vinyl ether.

% in the Examples always means % by weight.

EXAMPLES (1) 80 g of CuCl and 96 g of N,N,N',N'-tetramethylethylenediamine were successively added under protective gas to 800 ml of acetonitrile in a glass autoclave which is provided with a stirrer, thermometer, manometer and gas-introduction tube with sintered disk, whereupon the solution, which is initially dark brown, assumes a bluegreen color. After the reactor had been closed and the gas had been flushed out with HFPO, gaseous HFPO was passed, while stirring vigorously at 25°–30° C., into the previously prepared catalyst solution, whereupon a pressure of 2.2–2.3 bar is set up. After 105 minutes the introduction of HFPO was stopped, the stirrer was switched off and the reaction mixture was given time to separate into two phases. The lower product phase (1178 g) was separated off and analyzed in the form of the methyl esters by gas chromatography. It contained 82.9% of 2-perfluoropropoxy-n-propionyl fluoride (see formula (I) with n=1), in addition to 10.2% of perfluoropropionyl fluoride ((I) with n=0) and 6.7% of the acid fluoride (I) with n=2.

(2) 60 g of CuCl and 72 g of N,N,N',N'-tetramethylethylenediamine were reacted in 1200 ml of acetonitrile in a reaction vessel equipped with a stirrer, an internal thermometer, a manometer, a sintered disk for introduction and a discharge valve at the bottom to give the blue-green catalyst solution. After the reaction vessel had been closed and the gas had been flushed out, gaseous HFPO was passed through the sintered disk for introduction into the catalyst solution at a rate of inflow such that a pressure of 0.4–0.6 bar is set up. The reaction temperature was maintained at 15°–19° C. by external cooling. After 210 minutes, the stream of gaseous HFPO was stopped, and the crude product (1118 g) was isolated as described in Example 1. The gas chromatogram of the methyl esters showed the following composition: 81.9% of compound (I) with n=1, 9.6% of (I) with n=0 and 8.5% of (I) with n=2.

The catalyst phase remaining in the reaction vessel was subsequently charged anew with gaseous HFPO, with the introduction of HFPO always being stopped when the reaction vessel had become 90% full. After the product and catalyst phases had separated and the product phase had been discharged through the discharge valve in the bottom into a collecting container, introduction of HFPO was continued. In this way, with a rate of HFPO inflow of 0.42 kg/hour, 31.3 kg of HFPO were passed into the catalyst solution at 14°–27° C. in 74 hours. The product was collected in 3 portions and analyzed.

|  | 1st Reaction phase (up to 21 hours) | 2nd Reaction phase (21–44 hours) | 3rd Reaction phase (44–72 hours) |
|---|---|---|---|
| (I) n = 0 | 12.0% | 11.0% | 12.4% |
| (I) n = 1 | 80.3% | 81.2% | 80.1% |
| (I) n = 2 | 7.4% | 7.2% | 7.4% |

(3) to (6) The process indicated in Example 1 followed. Table 1 indicates the conditions and the results achieved.

(7) to (9) Table 2 is a compilation of the batch amounts in the examples, which have been carried out as in Example 1, as well as the results obtained. Metal halides with various cations were employed as metal salts.

(10) to (13) Copper salts of various acids were employed as metal salts in accordance with Example 1. The reaction conditions and results are compiled in Table 3.

TABLE 1

| Example | Metal salt mole | Diamine mole | Solvent ml | Temperature °C. | Pressure bar | Reaction time minutes | Crude product g | GC Composition (%): | | |
|---|---|---|---|---|---|---|---|---|---|---|
| | | | | | | | | (I) n = 1 | (I) n = 0 | (I) n = 2 |
| 3 | CuCl 0.24 | TMMD 0.245 | CH₃CN 500 | 25.30 | 1.4 | 150 | 505 | 75.6 | 11.5 | 12.9 |
| 4 | CuCl 0.4 | TMED 0.41 | CH₃CN 800 | 30 | 0.9 | 105 | 893 | 77.3 | 9.7 | 13.0 |
| 5 | CuCl 0.15 | TMHD 0.15 | CH₃CN 300 | 20 | 1.8–2.0 | 390 | 1137 | 76.6 | 7.7 | 15.7 |
| 6 | CuCl | TEED | CH₃CN | 32 | 1.0 | 120 | 960 | 80.5 | 8.1 | 11.4 |

TABLE 1-continued

| Example | Metal salt mole | Diamine mole | Solvent ml | Temperature °C. | Pressure bar | Reaction time minutes | Crude product g | GC Composition (%): (I) n = 1 | (I) n = 0 | (I) n = 2 |
|---|---|---|---|---|---|---|---|---|---|---|
|  | 0.4 | 0.41 | 800 |  |  |  |  |  |  |  |

TMMD = N,N,N',N'-Tetramethylmethylenediamine
TMED = N,N,N',N'-Tetramethylethylenediamine
TMHD = N,N,N',N'-Tetramethylhexylidenediamine
TEED = N,N,N',N'-Tetraethylethylenediamine

TABLE 2

| Example | Metal salt mole | TMED mole | Solvent ml | Temperature °C. | Pressure bar | Reaction time minutes | Crude product g | GC Composition (%): (I) n = 1 | (I) n = 0 | (I) n = 2 |
|---|---|---|---|---|---|---|---|---|---|---|
| 7 | CuCl 0.4 | 0.41 | CH$_3$CN 800 | 12–20 | 0.4 | 330 | 1465 | 81.8 | 5.0 | 12.1 |
| 8 | CoF$_2$ 0.40 | 0.41 | CH$_3$CN 800 | 27 | 0.4 | 210 | 935 | 78.5 | 6.4 | 15.1 |
| 9 | ZnCl$_2$ 0.38 | 0.41 | CH$_3$CN 800 | 15 | 1.0 | 180 | 836 | 75.5 | 15.5 | 9.0 |

TMED = N,N,N',N'-Tetramethylethylenediamine

TABLE 3

| Example | Metal salt mole | TMED mole | Solvent ml | Temperature °C. | Pressure bar | Reaction time minutes | Crude product g | GC Composition (%): (I) n = 1 | (I) n = 0 | (I) n = 2 |
|---|---|---|---|---|---|---|---|---|---|---|
| 10 | CuCl 0.4 | 0.41 | CH$_3$CN 800 | 15 | 0.3 | 135 | 928 | 81 | 6.3 | 12.7 |
| 11 | CuCN 0.57 | 0.60 | CH$_3$CN 600 | 26–28 | 1.5–1.9 | n.d. | 627 | 80 | 4.0 | 14.0 |
| 12 | CuSCN 0.62 | 0.60 | CH$_3$CN 600 | 15–19 | 0.8–1.8 | n.d. | 623 | 78 | 11.0 | 12.0 |
| 13 | CuAc 0.2 | 0.2 | CH$_3$CN 200 | 20 | 1.9 | n.d. | 426 | 65 | 7.5 | 24.0 |

TMED = N,N,N',N'-Tetramethylethylenediamine
AC = Acetate
n.d. = not determined

We claim:

1. A process for the dimerization of hexafluoropropene oxide, which comprises the oligomerization of hexafluoropropene oxide to give the perfluorinated carbonyl fluorides of the general formula

$$C_2F_5(CF_2-O-\overset{\underset{\displaystyle CF_3}{|}}{CF})_nCOF \qquad (I)$$

in which n substantially represents the number 1, being carried out in an aprotic polar solvent in the presence of a catalyst which is composed of a metal salt of the elements of the 1st transition metal series of the periodic table and of a tertiary diamine of the general formula $$R^1R^2N\text{-}R\text{-}NR^3R^4 \qquad (II)$$

in which R represents an unbranched or branched, saturated or unsaturated hydrocarbon radical which has 1 to 12 carbon atoms, $R^1$ to $R^4$ are, independently of one another, cyclic or acyclic saturated or unsaturated hydrocarbon radicals which have 1 to 12 carbon atoms.

2. The process as claimed in claim 1, wherein fluorides, chlorides, bromides, iodides and cyanides, thiocyanates or acetates of iron, cobalt, nickel, copper or zinc are employed as metal salts.

3. The process as claimed in claim 1, wherein an aliphatic nitrile having 2 to 8 carbon atoms, an aliphatic dinitrile having 5 to 8 carbon atoms, an ether of the formula

$$R'\text{-}(O\text{-}CH_2CHR'')_xOR'$$

in which R' denotes an alkyl group having 1 to 4 carbon atoms, R" denotes hydrogen or methyl and x denotes an integer from 1 to 6, or a cyclic ether is used as aprotic polar solvent.

4. The process as claimed in claim 1, wherein R contains at least one hetero chain member or at least one hetero substituent which is inert toward the reaction components.

5. The process as claimed in claim 1, wherein $R^1$ to $R^4$ each contain at least one hetero chain member or at least one hetero substituent which is inert toward the reaction components.

6. The process as claimed in claim 1, wherein each two of the radicals $R^1$ to $R^4$ being linked via a hydrocarbon radical or at least one hetero atom.

7. The process as claimed in claim 2, wherein CuCl, CuCl$_2$, CoF$_2$, CoCl$_2$ or ZnCl$_2$ are employed.

8. The process as claimed in claim 3, wherein acetonitrile is used as aprotic polar solvent.

9. The process as claimed in claim 1, wherein the metal salt and the tertiary diamine (II) are employed in the molar ratio of 2:1 to 1:2.

10. The process as claimed in claim 9, wherein the molar ratio is 1:1.

11. The process as claimed in claim 1, wherein the oligomerisation is carried out at temperatures between 0° and 50° C.

12. The process as claimed in claim 11, wherein the oligomerisation temperature is between 5° and 35° C.

13. The process as claimed in claim 1, wherein the metal salt and the tertiarydiamine form a metal salt/diamine complex and the concentration of this metal salt/diamine complex in the solvent is 0.2 to 1.2 mole of metal salt and of diamine per liter of solvent.

14. The process as claimed in claim 1, wherein the reaction is carried out under atmospheric pressure or elevated pressure of between 0.5 and 3.5 bar.

15. The process as claimed in claim 1, wherein in the diamine (II) the radical R has 1 to 4 carbon atoms and the radicals $R^1$ to $R^4$ have 1 to 6 carbon atoms.

16. The process as claimed in claim 4 wherein oxygen or nitrogen is present as hetero atom, hetero substituent or hetero chain member.

17. The process as claimed in claim 5 wherein oxygen or nitrogen is present as hetero atom, hetero substituent or hetero chain member.

* * * * *